United States Patent [19]

Gerecht

[11] 4,089,868

[45] May 16, 1978

[54] SULFONIUM SALT SUBSTANTIVE SUNSCREEN MATERIALS

[75] Inventor: John Fred Gerecht, Somerville, N.J.

[73] Assignee: Colgate-Palmolive Company, New York, N.Y.

[21] Appl. No.: 538,690

[22] Filed: Jan. 6, 1975

Related U.S. Application Data

[60] Division of Ser. No. 148,158, May 28, 1971, Pat. No. 3,864,474, which is a continuation-in-part of Ser. No. 820,280, Apr. 29, 1969, abandoned, which is a continuation-in-part of Ser. No. 492,316, Oct. 1, 1965, abandoned.

[51] Int. Cl.² .................................................. C07D 249/20
[52] U.S. Cl. ........................ 260/308 B; 260/556 AR; 260/558 S
[58] Field of Search ......... 260/558 S, 556 HR, 308 B; 424/60

[56] References Cited

U.S. PATENT DOCUMENTS 3,318,953  5/1967  Wehrmeister .................... 260/558 S Primary Examiner—Paul M. Coughlan, Jr.
Attorney, Agent, or Firm—Richard N. Miller; Murray M. Grill; Herbert S. Sylvester

[57] ABSTRACT

A highly substantive sulfonium salt sunscreening agent represented by the formula:

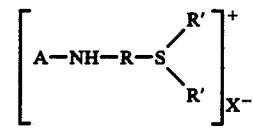

wherein
  A is a sunscreening moiety, having a prominent spectral absorption peak within the range of 250–400 millimicrons;
  R represents alkylene of from 2 to 18 carbon atoms;
  R' and R" represent alkyl, and wherein the sum of the carbon atoms in R' and R" is not less than 9 and not greater than 27, and wherein the nitrogen is linked to A as a carboxamido or sulfonmido group, and X is an anion.

16 Claims, No Drawings

SULFONIUM SALT SUBSTANTIVE SUNSCREEN MATERIALS

The present application is a divisional of U.S. Application Ser. No. 148,158, filed May 28, 1971, now U.S. Pat. No. 3,864,474, which is a continuation-in-part of abandoned U.S. Application Ser. No. 820,280, filed Apr. 29, 1969, which is a continuation-in-part of abandoned U.S. Application Ser. No. 492,316, filed Oct. 1, 1965.

The present invention relates to sunscreening agents and more particularly to sunscreening agents having improved adhesion to the skin.

Contrary to common belief the benefits of exposing the human body to sunlight are more psychological than physiological. Although a suntanned body is admired as synonymous with good health in this part of the world, it is probably more of a status symbol than a sign of physical fitness. It is said that in tropical agricultural countries where the working class must expose itself to the sun, a milk white skin rather than a "healthy tan" is considered desirable. Furthermore, reports on the harmful effects of sunlight on human skin have appeared in the medical literature. In a report of the Committee on Cosmetics to the American Medical Society [J. Am. Med. Assn. 161 1480-3 (1956); B. M. Kesten, J. Am. Med. Assn. 161 1565-7 (1956)], these effects are reported. Chronic exposure to sunlight is considered by Knox et. al. [J. M. Knox; J. Guin; and E. G. Cockerell, J. Invest. Dermatology 29 435-44 (1957); J. M. Knox, Am. Perfumer Aromat. 75 No. 8 42-4 (1960); J. M. Knox; A. C. Griffin; and R. E. Hakin, J. Invest. Dermatology 34 51 (1960); J. M. Knox, J. Soc. Cosmetic Chem. 13 119-24 (1962)] to be one of the major factors in the production of both cancerous conditions of the skin and the visible degenerative changes that occur with aging. Through Consumer Reports (Consumer Reports, 1961 p. 397) the general public have been warned of the dangers of sunbathing.

The tanning of the skin when exposed to sunlight is part of nature's method of protecting the individual from the harmful effects of ultraviolet radiation including sunburn. Tanning is a result of several processes which are not well understood. Rothman [S. Rothman Physiology and Biochemistry of the Skin, U. of Chicago Press, p. 552 (1954)] indicates that formation of new melanin, brownish pigment of the skin, migration of new melanin to the surface and oxidative darkening of preformed melanin all play a role. The former process is said to be brought about by the erytheme-producing radiation having a wave length between 2800 and 3100 A and the latter darkening produced by radiation between 3000 and 4200 A with a maximum effect as 3400 A. The necessity of erythemal radiation for new melanin formation has been questioned in recent reports [(a) M. A. Pathak; P. C. Riley; T. R. Fitzpatrick; and W. L. Curwen, Nature 193 148–50 (1962) (b) M. A. Pathak; F. C. Riley; and T. E. Fitzpatrick, J. Invest. Parmatology 39 435–43 (1962)], and evidence is presented to indicate that melanin formation also is induced by long wave ultraviolet and even visible light.

The chemical structure of melanin is not known but is formed by the oxidation of tyrosine catalyzed by the enzyme tyrosinase probably via the following sequence:

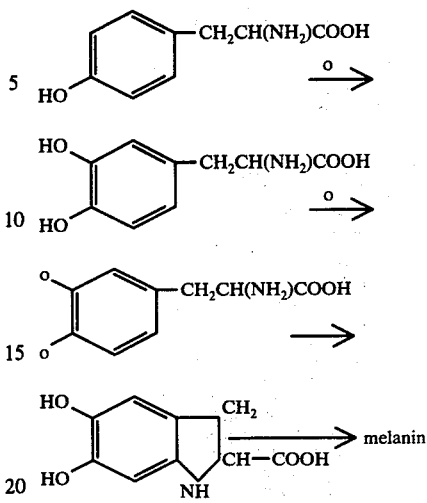

[(a) L. F. and M. Fieser, Advanced Organic Chemistry, Reinhold p. 1065-7 (1961) (b) R. A. Nicolauc and M. Piattelli, J. Polymer Science 58 1133-9 (1962)].

The outer horny layer of the skin, the stratum corneum, also thickens after exposure to sunlight. This layer is highly ultraviolet absorbing and is thought to offer considerable protection to the ultraviolet sensitive lower layers of the skin [B. M. Kesten, J. Am. Med. Assn. 161 1565-7 (1956)].

In addition, human perspiration contains urocanic acid,

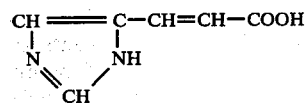

which is claimed to be a naturally occuring sunscreen. This compound shows an ultraviolet absorption between 2500 and 3000 A, the erythemal range, and is stated to be a natural defense against sunlight [(a) I. M. Hais and A. Zenisek, Am. Perfumer and Aromat. 74 Sept. 1959 p. 26-8 (b) A. Zenisek, J. A. Kral and I. M. Hais, Biochem. Biophysica Acta 18 589 (1955)].

"Sunscreens," synthetic compounds that absorb strongly in the ultraviolet region of the spectrum, have found wide use as protective agents against sunburn or erythema. Of the many compounds which have been tried over the years [E. G. Klarmann, Am. Perf. and Essential Oil Rev. 58 33-8 126-35 (1949)] derivatives of salicylic acid, p-aminobenzoic acid, 2-hydroxybenzophenone and 2-hydroxyohenylbenzotriazole have emerged as the most desirable "sunscreens" from the practical as well as theoretical point of view. However, as yet, no product is available which through regular use would impart convenient and constant protection against the damaging effects of ultraviolet radiation.

At least as early as 1946 it was recognized that one of the deficiencies of then existing "sun-tan" lotions was failure to protect because the sunscreening agent was diluted or floated off by perspiration. Resistance to water or sweat can be imparted to a degree by incorporating water repellents or emollients in the formulations. However, for various purposes such as more than occasional use and for incorporation in a variety of products it is advantageous to have as an active agent or agents in a formulation materials which not only absorb erythemal radiation but also adhere strongly to the skin.

Many compounds capable of absorbing ultraviolet radiation have been described in the literature and recommended as sunscreening agents. Among those recommended are the following:

| TYPE | SPECIFIC FORM |
|---|---|
| Aminobenzoic acids | o- and p-aminobenzoates and anthranilates |
| hydroxybenzoic acids | salicylates and tannates |
| Cinnamic acid | methyl and benzyl esters |
| Coumarine | unbelliferones; quercetin; enoulin; daphnin |
| Biphenyls: | o- and p-dihydroxybiphenyl disulfonates |
| Naphthols | sulfonates and carboxylates |
| Benzothiazoles | condensations of aromatic aldehydes and aminothiophenol |
| Imidazoles | uric acid and histidine derivatives; urocanic acid |
| "Sulfa" drugs | n',n'-Dimethyl-n$^4$-sulfanilyl-sulfanilamide; n$^4$-sulfanilyl-sulfanilamide |
| Aromatic ketones | benzalacetone; butyl-cinnamyl pyruvate |
| benzotriazoles | 2-hydroxyphenyl benzotriazole |
| cyano acrylates | ethyl α-cyano-B, B-diphenyl acrylate |
| dinitriles | B, B-diphenyl methylene malononitrile |
| Piperonals | |
| Benzophenones | Highly purified, light yellow, powdered benzophenones, e.g., 2, 2'-dihydroxy-4, 4'-dimethoxy-benzophenone |
| Hydrocarbons | stilbenes |
| Miscellaneous | acetanilide - Vitamin C |

Most of the foregoing and other materials having the capability of absorbing ultraviolet light have not proved satisfactory for use as sunscreen agents for one or more of the following reasons: cost, safety, discoloration of fabrics among others. Some are not sufficiently selective between erythemal and tanning radiation. In spite of the deficiencies of the presently recognized sunscreening agents the most widely used at the present time are derivatives of aminobenzoic acid, salicylic acid, and the substituted benzophenones marketed under the tradename, "Uvinul."

The sunscreen agents of the present invention combine in one molecule at least one sunscreen moiety such as enumerated hereinbefore and at least one substrate-binding moiety, such as

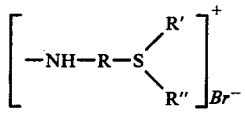

The present invention provides sulfonium salt substantive sunscreening materials conforming to the formula:

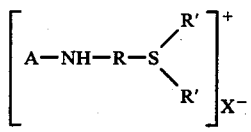

wherein A is a sunscreen moiety of the type enumerated hereinbefore and having a prominent special absorption peak within the range of 250–400 millimicrons, such as H$_2$NC$_6$H$_4$CO—, HOC$_6$H$_4$CO—, 2,4-dihydroxy-5-sulfo-benzophenone, etc.;

R represents alkylene of from 2 to 18 carbon atoms;
R' and R" represent alkyl groups of 7 to 26 and 1 to 4 carbon atoms respectively and wherein the sum of the carbon atoms in R' and R" is not less than 9 and not greater than 27; and wherein the nitrogen is linked to A as a carboxamide or sulfonamido group; and X is an anion such as Br, Cl, I, C$_2$H$_5$SO$_4$, CH$_3$COO—, and CH$_3$SO$_4$.

It will be understood that substituents, R, R' and R" in the above-depicted formula may contain further substituent groups of an inert, innocous nature, the sole requirement imposed being that any such group be devoid of any tendency to affect the essential properties of the parent compound, deleteriously, i.e., such properties as radiation absorption, substantivity, etc. Thus, R may be substituted with, for example, alkyl, cycloalkyl, alkoxy, hydroxy, cyano and halogen. Moreover, R' and R" may be substituted alkyl, hydroxyalkyl, alkoxyalkyl, cyanoalkyl, alkoxyalkyl, carbalkoxy alkyl, etc.

The sulfonium salts of the present invention may be readily and easily prepared according to numerous techniques. Thus, the aminoalkyl-alkylthioethers, for example, the aminopropyl octyl thioether can be prepared by cyanoethylation ("Organic Reactions" Volume V) of octyl mercaptan followed by lithium-aluminum hydride reduction ("Organic Reactions" Volume VI) of the cyano groups to a primary amine. Thus, for example, 3,-(p-nitrobenzamido) propyl octyl thioether is prepared as follows: 10.2 grams of 3-aminopropyl octyl thioether are dissolved in 15 milliliters of pyridine and 9.3 grams of p-nitrobenzoyl chloride are added in small portions at about 25° C. (77° F.). When all of the acid chloride has been added the resulting reaction mixture is heated on a steam bath for about 0.5 hours cooled to room temperature and poured into water. The product is taken up in diethyl ether. The ether solution is washed with dilute aqueous sodium carbonate solution, then with dilute hydrochloric acid and finally with water. The washed ethereal solution is dried over magnesium sulfate and the ether evaporated. The residue is crystallized from 50 milliliters of 2-propanol. 15 grams (86% yield) of 3-(p-nitrobenzamido)propyl octyl thioether having a melting point of 67.5° to 69° C. (153.5° to 156.2° F.) are recovered.

The sulfonium salts of the thioethers are readily prepared in any suitable manner as for example by reacting the thioether with methyl bromide or dimethyl sulfate. Thus, the sulfonium salt of the aforedescribed 3-(p-nitrobenaamido) propyl octyl thipether is prepared as follows: 15.6 grams of 3-(p-nitrobenzamido)propyl octyl thioether and 12.0 grams of methyl bromide are mixed in a small pressure bottle and held at room temperature, i.e., about 72° F. (22.2° C.) for about three days. The pressure is then released and the residue dissolved in a mixture of 50 milliliters of ethyl acetate and 2 milliliters of 2-propanol. The crystals which separate in the refrigerator (at about 5° C.) are separated from the mother liquor on a suction funnel. 17.5 grams (87.1% yield) of the sulfonium bromide of the thioether are recovered. The sulfonium salt melts at 93° to 95° C. (199.4° to 203.0° F.) and has an equivalent weight by silver nitrate titration of the bromide ion of 445.4 grams. The calculated equivalent weight for 3-(p-nitrobenzamido propyl-methyl-octyl sulfonium bromide, O$_2$NC$_6$H$_4$CONH(CH$_2$)$_3$CH$_3$S$^+$(CH$_2$)$_7$ CH$_3$Br$^-$is 447.5.

An alternative method for the synthesis of the compounds contemplated herein employs as the starting material an aminoalkylene mercaptan. The series of reactions involved can be represented as follows:

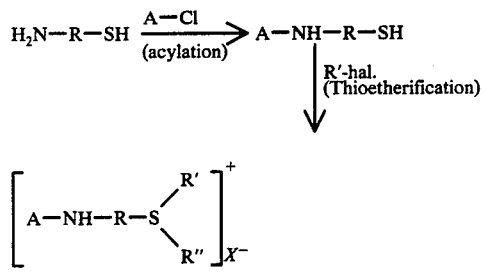

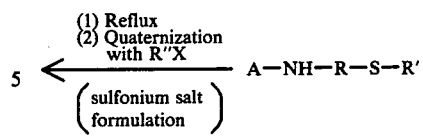

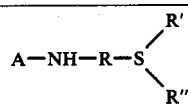

Thus, according to foregoing sequence of step, the sunscreening moiety is initially provided in the form of its acyl halide derivative e.g., sulfonyl or carboxyl chloride and thereafter derivatized as illustrated. Specific examples of compounds found to be particularly beneficial in the practice of the present invention include the following:

$$A-NH-R-S\overset{R'}{\underset{R''}{\diagdown}}$$

| Compound No. | A | R | R' | R'' | X⁻ |
|---|---|---|---|---|---|
| I | $O_2N-\phenyl-CO-$ | $(CH_2)_3$ | $C_8H_{17}$ | $CH_3-$ | Br |
| II | " | " | $C_{12}H_{25}$ | " | " |
| III | $\phenyl(OH)-CO-$ | " | $C_8H_{17}$ | " | " |
| IV | " | " | $C_{12}H_{25}$ | " | " |
| V | " | $(CH_2)_6$ | " | $C_2H_5-$ | Cl |
| VI | " | $(CH_2)_9$ | $C_{10}H_{21}$ | $C_3H_7-$ | " |
| VII | " | $(CH_2)_{13}$ | $C_{14}H_{29}$ | $C_2H_5-$ | " |
| VIII | " | $(CH_2)_{10}$ | $C_{22}H_{45}$ | $CH_3-$ | $CH_3SO_3$ |
| IX | $O_2N-\phenyl-SO_2-$ | $(CH_2)_{11}$ | $C_9H_{19}$ | $C_2H_5-$ | I |
| X | $H_2N-\phenyl-CO-$ | $(CH_2)_2$ | $C_8H_{17}$ | $CH_3-$ | $CH_3COO$ |
| XI | $H_2N-\phenyl-CO-$ | $(CH_2)_9$ | $C_{12}H_{25}$ | $CH_3-$ | $CH_3COO$ |
| XII | $H_2N-\phenyl-SO_2-$ | $(CH_2)_9$ | $CH_{12}H_{25}$ | $CH_3-$ | Cl |
| XIII | $\phenyl(OH)-SO_2-$ | $(CH_2)_{16}$ | $C_{15}H_{31}$ | $C_2H_5-$ | Cl |
| XIV | $O_2N-\phenyl-CO-$ | $(CH_2)_3CH(CH_3)(CH_2)_6$ | $C_8H_{17}$ | $CH_3-$ | Br |
| XV | $H_2N-\phenyl-SO_2-$ | $(CH_2)_5CH(C_2H_5)(CH_2)_9$ | $C_8H_{17}$ | $CH_3-$ | $CH_3SO_4$ |
| XVI | $O_2N-\phenyl-CO_2-$ | $(CH_2)_3CH(CH_3)(CH_2)_3$ | $C_{10}H_{21}$ | $C_2H_5-$ | $CH_3SO_4$ |
| XVII | " | $(CH_2)_{11}$ | $CH_{14}H_{29}$ | $CH_3-$ | I |
| XVIII | " | $(CH_2)_{13}$ | $C_{13}H_{27}$ | $CH_3-$ | $CH_3SO_4$ |
| XIX | $H_2N-\phenyl-SO_2-$ | $(CH_2)_3$ | $C_9H_{19}$ | $CH_3-$ | $CH_3SO_4$ |
| XX | " | $(CH_2)_{12}$ | $C_{16}H_{33}$ | $C_2H_5-$ | " |
| XXI | $O_2N-\phenyl-CO-$ | $(CH_2)_8$ | " | " | $CH_3COO$ |
| XXII | $\phenyl(OH)-CO-\phenyl-CO-$ | $(CH_2)_3$ | $C_{11}H_{23}$ | $C_4H_9-$ | " |
| XXIII | " | $(CH_2)_6$ | $C_8H_{17}$ | $CH_3-$ | Cl |
| XXIV | " | $(CH_2)_{10}$ | $C_{12}H_{25}$ | " | " |
| XXV | " | $(CH_2)_{16}$ | $C_{14}H_{28}$ | " | " |

-continued $$A-NH-R-S\diagdown_{R''}^{R'}$$

| Compound No. | A | R | R' | R" | X⁻ |
|---|---|---|---|---|---|
| XXVI |  | ─(CH₂)₄─ | C₉H₁₉─ | " | Br |
| XXVII | " | ─(CH₂)₁₂─ | C₁₂H₂₅─ | " | Cl |
| XXVIII | 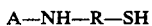 | ─(CH₂)₂─ | C₈H₁₇─ | " | " |
| XXIX | " | ─(CH₂)₉─ | C₁₀H₂₁─ | " | " |
| XXX | " | ─(CH₂)₁₂─ | C₁₂H₂₅─ | C₂H₅─ | C₂H₅SO₄ |
| XXXI | " | ─(CH₂)₇─CH─(CH₂)₃─<br>              │<br>              CH₃ | C₁₄H₂₉─ | " | CH₃SO₄ |
| XXXII | [structure: benzene-N=N-C₆H₄(OH)-CO─] | ─(CH₂)₅─ | C₇H₁₅─ | C₂H₅─ | CH₃SO₄ |
| XXXIII | " | ─(CH₂)₃CH(CH₃)(CH₂)₄─ | C₉H₁₉─ | CH₃─ | CH₃COO |
| XXXIV | " | ─(CH₂)₈─ | C₁₁H₂₃─ | C₂H₅─ | CH₃COO |

A further aspect of the present invention contemplates the provision of novel thioether compounds having the following structural formula:

A—NH—R—S—R' wherein A, R and R' have the significance delineated hereinbefore; the value of R' in such compounds varies preferably from 7 to 26 carbon atoms. As more fully explained hereinbefore, compounds of this type are obtained via thioetherification of the intermediate mercaptan compound with an alkyl halide. The thioetherification reaction product may then be converted to the corresponding sulfonium salt by simple quaternization.

The intermediate mercaptan compounds as represented by the formula

A—NH—R—SH

A and R having the significance hereinbefore explained likewise appear to be novel compounds and, of course, comprise a still further aspect of the subject invention. These compounds are of course obtained via acylation of an aminoalkylene mercaptan, with the compound A—Cl, which may also be represented as A—SO₂Cl or A-COCl.

The testing of compounds for substantivity to skin presents some problems. The most apparent difficulty is the limited availability of human skin. Hence, a material for use as a substrate for controlled evaluation of the substantive as well as the sunscreening properties of the essential ingredient of a sunscreening composition. Human hair was selected as the best material for the following reasons:
1. It is readily available.
2. It bears a strong relation to the outer layer of skin, the stratum corneum; hydrogen bonds, salt linkages and Van der Waal's forces are considered to play similar roles in both hair and epidermal keratin [W. Montagna and R.A. Ellis, The Biology of Hair Growth, p. 147, Academic Press (1958)].
3. Although its protein structure is not completely known, it is much better characterized chemically than the stratum corneum.

PREPARATION OF HAIR

Approximately 50 gram hanks of untreated De Meo brown hair (from De Meo Brothers, New York City) were cut into one-fourth – one-half inch long clippings with an electric clipper. Each 50 gram hair batch was washed once with 2500 ml. of a 1.0 percent sodium bicarbonate solution by stirring vigorously for about two hours and then leaving it soak overnight. The sodium bicarbonate wash was then decanted and the hair was given six consecutive rinses with 2500 ml. portions of deionized water by stirring vigorously for ten minutes, settling for 15 to 20 minutes and decanting. The sixth water rinse gave 97.5 – 99 percent light transmission in the 280 – 320 mu range determined with a Beckman DU quartz spectrophotometer. After decantation of the sixth water rinse, the hair was transferred to a Buchner funnel, broken up into small clumps or mats, and allowed to drain overnight. The bulk of the remaining surface water was removed by pressing the hair mats between paper towels. The last traces of surface water were removed by mechanically breaking down the hair mats into the individual fibers and blotting dry between sheets of filter paper. The hair was then transferred to a 66 percent humidity chamber, over saturated sodium nitrite solution, and conditioned for a minimum period of one week after which it was stored in a screw-capped glass jar until used.

METHOD OF MEASUREMENT

The standard procedure was to soak one gram samples of hair clippings (conditioned as described above) in a 10 ml. portion of a solution of the substantive agent in buffer and in a 10 ml. portion of the corresponding buffer (blank) for a period of exactly one hour. The solution and the buffer were then pipetted off of the hair samples and diluted with the original buffer. The solution was diluted to an appropriate concentration for ultraviolet light (UV) absorption measurement and the buffer (blank) was diluted in the same proportion as the solution. UV absorption measurements were run on the diluted solutions and on an equivalent dilution of the original solution of substantive agent with the buffer using a Cary automatic recording spectrophotometer in the 250 – 350 mu range.

The Cary UV apparatus continuously records the absorbance (A) of the solution, which is directly proportional to the amount of UV absorbing material in solution. Pickup of the substantive agent by the hair lowers the concentration of material in the solution resulting in a proportionate decrease in the absorbance. The amount of substantive material picked up by the hair was calculated from the decrease in absorbance (at peak absorption) resulting from contact with the hair corrected by the increase in absorbance of the corresponding buffer solution (blank) due to contact with the hair for the same length of time.

The following Examples are given for purposes of illustration only and are not intended to constitute a limitation on the present invention. All parts and percentages given are by weight unless otherwise indicated. In each of the procedures exemplified, the following sequence of operations is observed.

One gram of hair prepared as described hereinbefore is treated for 1 hour at pH 7.12 with 10 milliliters of an 0.1 percent solution of the sulfonium compound in a 0.065 molar solution of triethanolamine buffer. The hair is separated from the solution and the solution analyzed for a decrease in the concentration of the sulfonium compound by ultra-violet absorption at the maximum before and after contact with the hair. The data so obtained are set forth in Table 1.

| Ex. No. | Sulfonium Compound No. |
|---|---|
| 25 | XXV |
| 26 | XXVI |
| 27 | XXVII |
| 28 | XXVIII |
| 29 | XXIX |
| 30 | XXX |
| 31 | XXXI |
| 32 | XXXII |
| 33 | XXXIII |
| 34 | XXXIV |

In each of the above examples, the results obtained are similar to those described in connection with Examples 1–4, i.e., the sulfonium compounds exhibit excellent substantivity characteristics.

While the foregoing aqueous solutions containing .1% of sulfonium salt substantive sunscreening agent are sunscreening compositions effective for protection from ultraviolet radiation, other suitable carriers may be substituted for water. The identity of the sunscreening carrier or vehicle is determined by the final form of the sunscreening composition--solid, solution, lotion, cream, ointment, and aerosol--and such carriers are well known to those skilled in the art. Such carriers are characterized by compatibility with the sulfonium salt agent and the skin as well as nontoxicity. Suitable carriers include water; $C_2$–$C_4$ alcohols such as isopropanol, ethanol, propylene glycol, and glycerol; fatty material such as high molecular weight paraffin, hydrocarbons

| Ex. No. | Compound | MP °C. | Eq. Wt. Found | Wt. Calc. | Wavelength of Maximum Absorbance A | Mg. Avail. | Comp. Picked Up | % Picked Up |
|---|---|---|---|---|---|---|---|---|
| 1 | 3-Salicylamido-propyl-methyl-octyl-sulfonium bromide. | 100°–101° | 413.5 | 418.5 | 3000 | 10 | 5.19 | 51.9 |
| 2 | 3-Salicylamido-propyl-methyl-dodecyl-sulfonium bromide. | 82–84° | 472.0 | 474.6 | 3000 | 10 | 9.10 | 91.0 |
| 3 | 3-(p-nitrobenzamido) propyl-methyl-octyl sulfonium bromide. | 93–95° | 445.7 | 447.5 | 2690 | 10 | 4.99 | 49.9 |
| 4 | 3-(p-nitrobenzamide) propyl-methyl-dodecyl bromide. | 76–77° | 502.0 | 503.0 | 2690 | 10 | 8.16 | 81.6 |

Examples 5–34

The procedure outlined in connection with Examples 1–4 is repeated except that the sulfonium salt compound is replaced in equivalent amounts with the following:

| Ex. No. | Sulfonium Compound No. |
|---|---|
| 5 | V |
| 6 | VI |
| 7 | VII |
| 8 | VIII |
| 9 | IX |
| 10 | X |
| 11 | XI |
| 12 | XII |
| 13 | XIII |
| 14 | XIV |
| 15 | XV |
| 16 | XVI |
| 17 | XVII |
| 18 | XVIII |
| 19 | XIX |
| 20 | XX |
| 21 | XXI |
| 22 | XXII |
| 23 | XXIII |
| 24 | XXIV |

(e.g., mineral oil and petrolatum), and vegetable oils (e.g., coconut, olive, and sesame oil); and combinations of the aforementioned carriers, with aqueous carriers being preferred. While as little as 0.1% of the sulfonium salt agent may be used, sunscreen compositions generally contain from 1 to 25% by weight of the sulfonium salt. For example, solutions containing one to twenty-five percent of the sulfonium salt in aqueous $C_2$ – $C_4$ alcohol containing five to 75 percent of water can be used for protection from ultraviolet radiation. Further, Examples 35–39. show that the sulfonium salts can be incorporated into typical water-in-oil or oil-in-water emulsions.

Example 35 (water-in-oil lotion)

| Component A | |
|---|---|
| Ingredient | Weight Percent |
| 3-salicylamido-propyl dodecyl methyl sulfonium bromide | 1 – 10 |
| Mineral oil+ | 32 – 23 |
| Beeswax | 1 |

-continued

Component A

| Ingredient | Weight Percent |
| --- | --- |
| Nonionic emulsifier* | 2 – 10 |

[30]It is preferred to use either extra-light mineral having a viscosity, Saybolt Seconds, in the range of 55 to 65 at 100° F. or extra heavy mineral oil having a viscosity, Saybolt Seconds, in the range of 340 to 355 at 100° F. However, a mineral oil having a viscosity between 55 and 355 Saybolt Seconds can be used.

*e.g., mixture of 37% of sorbitanmonostearate ("Arlacel 60"), 31.5% of polyoxyethylene-sorbitanmonostearate ("Tween 60"), and 31.5% of sorbitan sesquioleate ("Arlacel 83").

Component B

| Ingredient | Weight Percent |
| --- | --- |
| Water | 61 |
| Preservative | q.s. |

Component B is added to Component A at about 85° C. (185° F.) with agitation and perfume (q.s.) added to the mixture after cooling to about 30° to 50° C. (86° – 122° F.), whereby a water-in-oil sunscreening lotion is formed.

EXAMPLE 36 (oil-in-water lotion)

Component A

| Ingredient | Weight Percent |
| --- | --- |
| Mineral oil of 60 Universal Saybolt seconds viscosity | 25.0 |
| Nonionic emulsifiers* | 10.0 |

*preferably a mixture of 40% Arlacel 60 and 60% Tween 60.

Component B

| Ingredient | Weight Percent |
| --- | --- |
| Water | 61.5 |
| Preservative | q.s. |

Component C

| Ingredient | Weight Percent |
| --- | --- |
| 3-salicylamido-propyl dodecyl methyl sulfonium bromide | 3.5 |
| Perfume | q.s. |

A and B are heated to about 60° C. (140° F.) and mixed. Then C is added at about 30° to about 50° C. (86° to 122° F.) to form an oil-in-water sunscreening lotion composition.

EXAMPLE 37 (oil-in-water lotion)

Component A

| Ingredient | Weight Percent |
| --- | --- |
| Mineral Oil of 60 Universal Saybolt seconds viscosity | 25.0 |
| Nonionic emulsifiers* | 10.0 |

*preferably 40% Arlacel 60 and 60% Tween 60.

Component B

| Ingredient | Weight Percent |
| --- | --- |
| Water | 61.5 |
| Preservative | q.s. |

Component C

| Ingredient | Weight Percent |
| --- | --- |
| 3-salicylamido-propyl dodecyl methyl sulfonium bromide | 2.5 |
| 3-salicylamido-propyl-octyl methyl sulfonium bromide | 1.0 |
| Perfume | q.s. |

Component A

| Ingredient | Weight Percent |
| --- | --- |
| Mineral oil of 60 Universal Saybolt seconds viscosity | 25.0 |
| Nonionic emulsifiers* | 10.0 |

*preferably 40% Arlacel 60 and 60% Tween 60

Component B

| Ingredient | Weight percent |
| --- | --- |
| Water | 61.5 |
| Preservative | q.s. |

Component C

| Ingredient | Weight Percent |
| --- | --- |
| 3-(p-nitrobenzamido)propyl-methyl octyl sulfonium bromide | 3.5 |
| Perfume | q.s. |

Each of the emulsion systems prepared as described exhibits excellent substantivity and sunscreening characteristics and, due to their provision in emulsion form, is beneficially adapted for application to surfaces to be protected such as human skin. Similar results obtain when each of the sulfonium compounds described in Examples 36–39 is replaced in equivalent quantities with one or more of the other sulfonium compounds described herein, i.e., Compounds V through XXXIV inclusive. It will also be understood that the sulfonium compounds contemplated by the present invention may be employed in admixtures comprising 2 or more. In fact, such manner of proceeding provides a particularly effective embodiment since the advantageous properties characterizing a plurality of such materials may be diverted to useful purposes.

It will further be understood that the subject invention contemplates modification of a wide variety of sunscreening agents, regardless of chemical structure, the attachment to such compounds of the substrate-binding moiety more particularly defined hereinbefore, i.e.

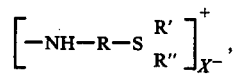

specific representatives of such sunscreening compounds including, without necessary limitation, coumarine, biphenyls, naphthols, imidazoles, piperonals, hydrocarbons, etc. Efficacious practice of the subject invention requires only that the basic sunscreening molecule as represented by "A" in the structural formula possesses a dominate spectral absorption within the 250-400 millimicron range.

What is claimed is:

1. A substantive sulfonium salt sunscreen agent represented by the formula:

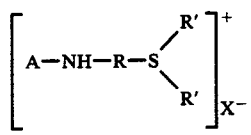

wherein A is a substituted benzene sunscreening moiety having a prominent spectral absorption peak within the range of 250-400 millimicrons and selected from the group consisting of

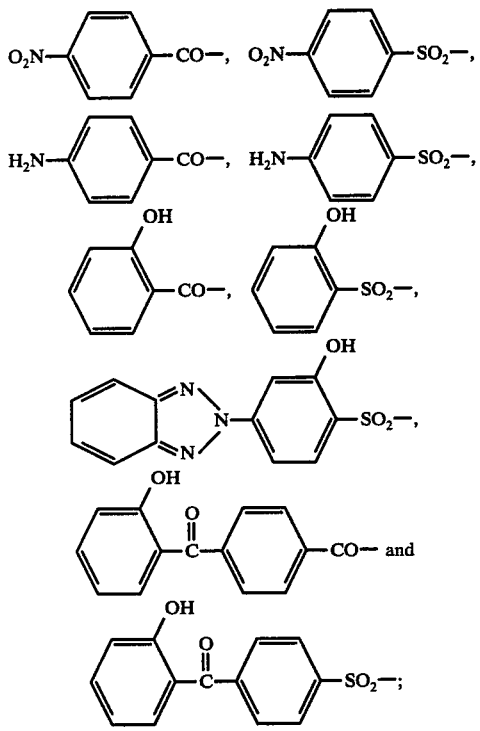

R represents alkylene of from 2 to 18 carbon atoms; R' represents alkyl of from 7 to 26 carbon atoms; R" represents alkyl of from 1 to 4 carbon atoms; the sum of the carbon atoms in R' and R" is not less than 9 and not greater than 27, and wherein the nitrogen is linked to A as a carboxamido or sulfonamido group, and X is selected from the group consisting of Br, Cl, I, $C_2H_5SO_4$, $CH_3CO_2$ and $CH_3SO_4$.

2. A sunscreening agent according to claim 1 wherein A is selected from the group consisting of nitrobenzoyl, hydroxybenzoyl, benzophenanyl, and hydroxybenzotriazolyl, wherein R represents $—(CH_2)_3$, R' represents $C_8H_{17}—$ or $C_{12}H_{25}—$, and R" represents $CH_3—$.

3. A sunscreening agent according to claim 2 wherein R' is $C_{12}H_{25}—$ and X is Br.

4. A sunscreening agent according to claim 2 wherein R' is $C_8H_{17}—$ and X is Br.

5. A sunscreening agent in accordance with claim 1, wherein said moiety a derivative of benzoic acid and is linked to the nitrogen as a carboxamido group.

6. A sunscreening agent in accordance with claim 5 wherein said moiety is

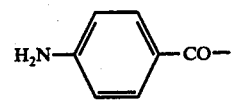

7. A sunscreening agent in accordance with claim 5 wherein said moiety is

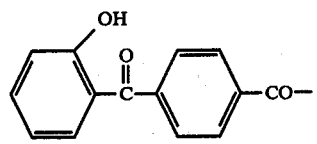

8. A sunscreening agent in accordance with claim 5 wherein said moiety is

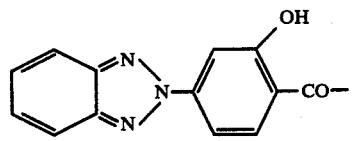

9. A sunscreening agent in accordance with claim 5 wherein said moiety is

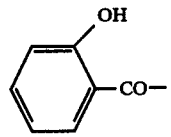

10. A sunscreening agent in accordance with claim 5 wherein said moiety is

11. A sunscreening agent in accordance with claim 1 wherein said moiety a is linked to the nitrogen as a sulfonamido group.

12. A sunscreening agent in accordance with claim 11 wherein said moiety is a

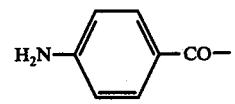

13. A sunscreening agent in accordance with claim 11 wherein said moiety is

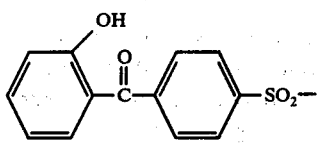
14. A sunscreening agent in accordance with claim 11 wherein said moiety is
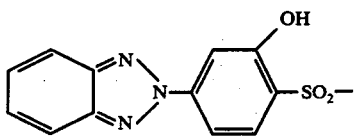
15. A sunscreening agent in accordance with claim 11 wherein said moiety is
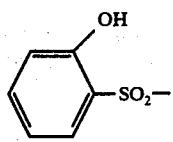
16. A sunscreening agent in accordance with claim 11 wherein said moiety is
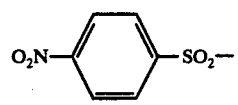
* * * * *